US011439628B2

(12) United States Patent
Sandner et al.

(10) Patent No.: US 11,439,628 B2
(45) Date of Patent: Sep. 13, 2022

(54) USE OF NON-STEROIDAL MINERALOCORTICOID RECEPTOR ANTAGONISTS ALONE OR IN COMBINATION FOR THE TREATMENT OF MUSCULAR OR NEUROMUSCULAR DISEASES

(71) Applicant: Bayer Aktiengesellschaft, Leverkusen (DE)

(72) Inventors: Peter Sandner, Wuppertal (DE); Peter Kolkhof, Wuppertal (DE); Ilka Mathar, Düsseldorf (DE); Stefanie Breitenstein, Düsseldorf (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 17/051,923

(22) PCT Filed: May 10, 2019

(86) PCT No.: PCT/EP2019/062021
§ 371 (c)(1),
(2) Date: Oct. 30, 2020

(87) PCT Pub. No.: WO2019/215317
PCT Pub. Date: Nov. 14, 2019

(65) Prior Publication Data
US 2021/0121447 A1   Apr. 29, 2021

(30) Foreign Application Priority Data
May 11, 2018   (EP) .................................... 18171857

(51) Int. Cl.
*A61P 21/04*   (2006.01)
*A61K 31/506*   (2006.01)
*A61K 31/4375*   (2006.01)

(52) U.S. Cl.
CPC ........ *A61K 31/4375* (2013.01); *A61K 31/506* (2013.01); *A61P 21/04* (2018.01)

(58) Field of Classification Search
CPC .... A61K 31/4375; A61K 31/506; A61P 21/04
USPC ....................................................... 514/300
See application file for complete search history.

(56) References Cited

U.S. PATENT DOCUMENTS

| 10,336,749 | B2 | 7/2019 | Platzek |
| 10,918,639 | B2* | 2/2021 | Kolkhof .................. A61P 43/00 |
| 2016/0324856 | A1* | 11/2016 | Long .................... A61B 5/4848 |
| 2019/0224176 | A1 | 7/2019 | Kolkhof et al. |
| 2019/0262340 | A1 | 8/2019 | Kolkhof et al. |

FOREIGN PATENT DOCUMENTS

| WO | 2015106268 A1 | 7/2015 |
| WO | 2017029261 A1 | 2/2017 |
| WO | 2017032673 A1 | 3/2017 |
| WO | 2018069126 A1 | 4/2018 |
| WO | 2018069148 A1 | 4/2018 |

OTHER PUBLICATIONS

Extended European Search Report of European Patent Application No. 18171857.8-1109, dated Nov. 23, 2018, filed by Applicant Bayer Aktiengesellschaft.
International Search Report and Written Opinion of International Patent Application No. PCT/EP2019/062021, dated Jun. 28, 2019, application filed May 10, 2019 by Applicant Bayer Aktiengesellschaft.
Adamo, C.M. et al., "Sildenafil reverses cardiac dysfunction in the mdx mouse model of Duchenne muscular dystrophy," PNAS, Nov. 2, 2010, vol. 107, No. 44, pp. 19079-19083.
Amazit, L. et al., "Finerenone Impedes Aldosterone-dependent Nuclear Import of the Mineralcorticoid Receptor and Prevents Genomic Recruitment of Steroid Receptor Coactivator-1*," The Journal of Biological Chemistry, Sep. 4, 2015, vol. 290, No. 36, pp. 71876-71889.
Baerfacker, L. et al., "Discovery of BAY 94-8862: A Nonsteroidal Antagonist of the Mineralocorticoid Receptor for the Treatment of Cardiorenal Diseases," ChemMedChem 2012, 7, pp. 1385-1403.
Booth, R.E. et al., "Staying Current, Aldosterone," Adv Physiol Educ, Mar. 2002, vol. 26, No. 1, pp. 8-20.
Chadwick, J.A. et al., "Mineralocorticoid receptors are present in skeletal muscle and represent a potential therapeutic target," The FASEB Journal, Nov. 2015, vol. 29, pp. 4544-4554.
Dutzmann, J. et al., "The novel mineralocorticoid receptor antagonist finerenone attenuates neointima formation after vascular injury," PLOS One, Sep. 2017, 12(9), pp. 1-13.
Edginton, A.N. et al., "Development and Evaluation of a Generic Physiologically Based Pharmacokinetic Model for Children," Clin Pharmacokinet, 2006, 45(10), pp. 1013-1034.
Evgenov, O.V. et al., "NO-independent stimulators and activators of soluble guanylate cyclase: discovery and therapeutic potential," Nature Reviews, Sep. 2006, vol. 5, pp. 755-768.
Grune, J. et al., "Steroidal and Nonsteroidal Mineralocorticoid Receptor Antagonists Cause Differential Cardiac Gene Expression in Pressure Overload-induced Cardie Hypertrophy," Cardiovasc Pharmacol, May 2016, vol. 67, No. 5, pp. 402-441.
Grune, J. et al., "Selective Mineralocorticoid Receptor Cofactor Modulation as Molecular Basis for Finerenone's Antifibrotic Activity," Hypertension, 2018, 71, pp. 599-608.
Judge, D.P. et al., "Pathophysiology and Therapy of Cardiac Dysfunction in Duchenne Muscular Dystrophy," Am J Cardiovasc Drugs, 2011, 11(5), pp. 287-294.

(Continued)

*Primary Examiner* — Yevgeny Valenrod
(74) *Attorney, Agent, or Firm* — Quarles & Brady LLP

(57) ABSTRACT

The present invention relates to non-steriodal mineralocorticoid receptor (MR) and the pharmacology of mineralocorticoid receptor antagonists (MR Antagonists, MRAs). In particular, the invention relates to the use of MRAs alone and in combination preferably in combination with sGC stimulators and/or sGC activators for preparation of medicaments for the prevention and/or treatment of muscular or neuromuscular diseases, especially for the treatment of Duchenne Muscular Dystrophy (DMD).

8 Claims, No Drawings

(56) References Cited

OTHER PUBLICATIONS

Kolkhof, P. et al., "Finerenone, a Novel Selective Nonsteroidal Mineralocorticoid Receptor Antagonist Protects From Rat Cardiorenal Injury," J Cardiovasc Pharmacol, 2014, 64, pp. 69-78.

Kolkhof, P. et al., "Nonsteroidal antagonists of the mineralcorticoid receptor," Current Opinion Nephrol Hypertens. 2015, vol. 24, No. 5, 417-424.

Leung, D.G. et al., "Sildenafil Does Not Improve Cardiomyopathy in Duchenne/Becker Muscular Systrophy," Ann Neurol., Oct. 2014, 76(4), pp. 541-549.

Lowe, J. et al., "Mineralocorticoid Receptor Antagonists in Muscular Dystrophy Mice During Aging and Exercise," J Neuromuscul Dis. 2018, 5(3), pp. 295-306.

Lowe, J. et al., "Similar efficacy from specific and non-specific mineralcorticoid receptor antagonist treatment of muscular dystrophy mice," J Neuromuscul Dis. 2016, 3(3), 395-404.

Martin, E.A. et al., "Tadalafil Alleviates Muscle Ischemia in Patients with Becker Muscular Dystrophy," Science Translational Medicine, Nov. 28, 2012, vol. 4, Issue 161, 1-9.

Mourkioti, F. et al., "Role of telomere dysfunction in cardiac failure in Duchenne muscular dystrophy," Nature Cell Biology, 2013, vol. 15, No. 8, pp. 895-904.

Nelson, M.D. et al., "PDE5 inhibition alleviates functional muscle ischemia in boys with Duchenne muscular dystrophy," Neurology, 2014, 82, pp. 2085-2091.

Percival, J.M. et al., "Evaluation of the Therapeutic Utility of Phosphodiesterase 5A Inhibition in the mdx Mouse Model of Duchenne Muscular Dystrophy," 2011, S.H. Francis et al. (eds.), Phosphodiesterases as Drug Targets, Handbook of Experimental Pharmacology 204, pp. 323-344.

Percival, J.M. et al., "Sildenafil reduces respiratory muscle weakness and fibrosid in the mdx mouse model of Duchenne muscular dystrophy," J Pathol 2012, 228, 77-87.

Pitt, B. et al., "The Effect of Spironolactone on Morbidity and Mortality in Patients with Sever Heart Failure," N Engl J Med, 1999, vol. 341, No. 10, pp. 709-717.

Pitt, B. et al., "Eplerenone, a Selective Aldosterone Blocker, in Patients with Left Ventricular Dysfunction after Myocardial Infarction," N Engl J Med, 2003, vol. 348, No. 14, pp. 1309-1321.

Rafael-Fortney, J.A. et al., "Early Treatment with Lisinopril and Spironolactone Preserves Cardiac and Skeletal Muscle in Duchenne Muscular Dystrophy Mice," Circulation, 2011, 124, pp. 582-588.

Ramachandran, J. et al., "Nitric oxide signalling pathway in Duchenne muscular dystrophy mice: up-regulation of L-arginine transporters," Biochem. J., 2013, 449, pp. 133-142.

Raman, S.V. et al., "Eplerenone for early cardiomyopathy in Duchenne muscular dystrophy: a randomised, double-blind, placebo-controlled trial," Lancet Neurol, 2015, 14, pp. 153-161.

Sacco, A. et al., "Short Telomeres and Stem Cell Exhaustion Model Duchenne Muscular Dystrophy in mdx/mTR Mice," Cell, 2010, 143, pp. 1059-1071.

Schmidt, H.H.H.W. et al., "NO- and Haem-Independent Soluble Gyanylate Cyclase Activators," cGMP: Generators, Effectors and Therapeutic Implications, Handbook of Experimental Pharmacology, 2009, 191, pp. 309-339.

Stasch, J-P. et al., "NO-independent regulatory site on soluble guanylate cyclase," Naturem vol. 410, Mar. 2001, pp. 212-215.

Stasch, J-P. et al., "Targeting the heme-oxidized nitric oxide receptor for selective vasodilatation of diseased blood vessels," The Journal of Clinical Investigation, 2006, vol. 116, No. 9, pp. 2552-2561.

Stasch, J-P. et al., "NO- and haem-independent activation of soluble guanylyl cyclase: molecular basis and cardiovascular implications of a new pharmacological principle," British Journal of Pharmacology, 2002, 136, pp. 773-783.

Stasch, J-P. et al., "NO-Independent, Haem-Dependent Soluble Guanylate Cyclase Stimulators," H.H.H.W. Schmidt et al. (eds.), cGMP: Generators, Effectors and Therapeutic Implications, Handbook of Experimental Pharmacology, 2009, 191, pp. 277-308.

Thomas, G.D., "Functional muscle ischemia in Duchenne and Becker muscular dystrophy," Frontiers in Physiology, Dec. 2013, vol. 4, Article 381, pp. 1-6.

Thomas, G.D. et al., "Treatment with a Nitric Oxide-Donating NSAID Alleviates Functional Muscle Ischemia in the Mouse Model of Duchenne Muscular Dystrophy," PLoS ONE, 2012, 7(11), pp. 1-8.

Victor, R.G. et al., "A phase 3 randomized placebo-controlled trial of tadalafil for Duchenne muscular dystrophy," Neurology, 2017, 89, 1811-1820.

Zaman, M.A. et al., "Drugs Targeting the Renin-Angiotensin Aldosterone System," Nature, 2002, vol. 1, pp. 621-636.

Anonymous, "2018 New Directions in Biology and Disease of Skeletal Muscle Conference," Jun. 25, 2018, pp. 1-25. Retrieved from the Internet on Oct. 31, 2018; https://com-pharm-myology.sites.medinfo.ufl.edu/files/2018/06/2018-New-Directions-Conference-Program-Book_Website.pdf.

Anonymous, "Report from the 2018 New Direction in Biology and Disease of Skeletal Muscle Conference," Cure Duchenne, Jun. 28, 2018. Retrieved from the Internet on Oct. 30, 2018, https://www.cureduchenne.org/blog/report-from-the-2018-new-direction-in-biology-and-disease-of-skeletal-muscle-conference/.

Myology Institute at University of Florida, "Advances in Skeletal Muscle Biology in Health and Disease," Mar. 6-8, 2019, Grant Writing Workshop and Poster Sessions. http://myology.institute.ufl.edu/.

* cited by examiner

USE OF NON-STEROIDAL MINERALOCORTICOID RECEPTOR ANTAGONISTS ALONE OR IN COMBINATION FOR THE TREATMENT OF MUSCULAR OR NEUROMUSCULAR DISEASES

CROSS REFERENCE TO RELATED APPLICATIONS

This application is the U. S. national stage entry under 35 U.S.C. 371 of PCT/EP2019/062021 filed May 10, 2019, which is incorporated by reference herein, which claims benefit of priority to European Patent App. No. 18171857.8 filed on May 11, 2018.

The present invention relates to non-steroidal mineralocorticoid receptor (MR) and the pharmacology of mineralocorticoid receptor antagonists (MR Antagonists, MRAs). In particular, the invention relates to the use of MRAs alone and in combination preferably in combination with sGC stimulators and/or sGC activators for preparation of medicaments for the prevention and/or treatment of muscular or neuromuscular diseases, especially for the treatment of Duchenne Muscular Dystrophy (DMD).

BACKGROUND OF THE INVENTION

Duchenne muscular dystrophy (DMD) is an X-linked recessive disorder that affects approximately 1 in 5000 newborn human males in whom absence of the sarcolemmal protein dystrophin causes degeneration of skeletal and cardiac muscle. Males with DMD develop cardiomyopathy and typically die in the third or fourth decade of life. Importantly, myocardial disease is developing in DMD patients long before left ventricular (LV) function becomes abnormal. Therefore, current guidelines recommend that well established heart failure drugs such as angiotensin-converting enzyme (ACE) inhibitors or angiotensin receptor blockers (ARB) should be given once there is evident left ventricular systolic dysfunction. However, despite these treatments, the ability to walk may be already lost as teenager, requiring a wheelchair. Breathing difficulties and heart disease usually start by age 20 and the current life expectancy is around 30 years. There is no cure and a substantial unmet medical need to improve and prolong life in muscular dystrophies and DMD patients.

The cyclic nucleotides, cyclic adenosine monophosphate (cAMP) and cyclic guanosine monophosphate (cGMP), were discovered decades ago and represent one of the most important second messenger pathway within cells. It is well established that the regulation of intra-cellular cGMP pools have substantial impact on physiology, and pathophysiology and is one basic principle of pharmacological intervention [Evgenov et al. Nat Rev Drug Discov. 2006 September; 5(9):755-68; Schmidt H H et al. Handbook of Experimental Pharmacology 2009 (191)].

Nitrates and PDE5 inhibitors (PDE5i) which could increase intra-cellular cGMP levels are therefore already approved therapies for Angina Pectoris, and Pulmonary Hypertension (PAH) or Erectile Dysfunction (ED), respectively. More recently discovered sGC stimulators can overcome significant limitations of Nitrates and PDE5i by direct stimulation of the soluble guanylate cyclase (sGC). The sGC stimulators like Riociguat are approved for the treatment of Pulmonary Hypertension (PAH) and Chronic Thromboembolic Pulmonary Hypertension (CTEPH) or are in late stage Phase III clinical development for the treatment of Heart Failure (HFrEF). Moreover, additional sGC stimulators are in earlier stages of clinical development and preclinical investigation including e.g. Hypertension (HTN), Chronic Kidney Diseases (CKD), Systemic Sclerosis (SSc), Cystic Fibrosis (CF), Sickle Cell Disease (SCD) and others. This very broad treatment potential of sGC stimulators underpins this very effective and broad pharmacological intervention strategy for various diseases. The sGC stimulators bind to the alpha subunit of the non-oxidized and heme-containing sGC which leads to NO-independent formation and increase of intracellular cGMP. In addition, the sGC stimulators enhance the NO-effect on cGMP when NO is bound to the sGC [Stasch J P et al., Nature 2001, 410:212-215; Stasch J P and Hobbs A J. Handb. Exp. Pharmacol. 2009, 191, 277-308]. If the heme group is removed from the soluble guanylate cyclase, the remaining catalytic basal activity of the heme-free enzyme cannot be anymore stimulated by the sGC stimulators and also not by NO [Evgenov O V, Pacher P, Schmidt P M, Haskó G, Schmidt H H, Stasch J P. Nat Rev Drug Discov. 2006 September; 5(9):755-68]. This observation is important since heme-free and oxidized forms of the sGC are preferentially present at diseases which are linked to ischemic and hypoxic conditions and oxidative stress. The current understanding is that under oxidative stress conditions, the $Fe^{2+}$ iron atom of the heme group is oxidized to $Fe^{3+}$ which destabilizes the binding of the heme group to the beta-subunit and renders the enzyme heme-free. With the discovery of BAY 58-2667 (Cinaciguat) a new chemical matter was identified which is able to activate heme-free sGC. Therefore BAY 58-2667 is the prototype of this class of sGC activators. Common characteristics of these substances are that the activation of the oxidized or heme-free enzyme is markedly higher than that of the heme-containing enzyme and that in combination with NO they have an additive effect on enzyme activation [Evgenov et al., ibid.; J. P. Stasch et al., Br. J. Pharmacol. 136 (2002), 773; J. P. Stasch et al., J. Clin. Invest. 116 (2006), 2552]. More recently also other classes of sGC activators have been discovered, different in chemical structures, different in pharmacokinetic and pharmacodynamics profiles, but also different in organ distribution.

It is well established that cGMP increase by sGC stimulators leads to relaxation of vascular smooth muscle cells and blood pressure decrease. However, other modes of actions beyond vasodilation and targeting the vascular smooth muscle cells are only partly understood and are currently under investigation. In recent years it became obvious that cGMP increase might have impact also on cardiomyocyte and skeletal muscle cell function. Moreover, alterations in the NO/cGMP system driven by NOS (NO-Synthase) could be involved in the pathology of neuromuscular disorders and muscular dystrophies. In line with this, it was published previously that i.e. NO donors and PDE5 inhibitors showed beneficial effects in nonclinical animal models of muscular dystrophies [Thomas G D et al., PLoS One. 2012; 7(11):e49350; Ramachandran J et al., Biochem J. 2013 Jan. 1; 449(1):133-42; Thomas G D et al., Front Physiol. 2013 Dec. 18; 4:381; Adamo C M et al. Proc Natl Acad Sci. 2010 Nov. 2; 107(44):19079-83; Percival J M et al., J Pathol. 2012 September; 228(1):77-87] or i.e. PDE5 inhibitor treatment was beneficial in patients with Duchenne Muscular Dystrophies (DMD) [Nelson M D et al., Neurology. 2014 Jun. 10; 82(23):2085-91] and Becker Muscular Dystrophy (BMD) [Martin E A et al., Sci Transl Med. 2012 Nov. 28; 4(162):162ra155]. However, recent clinical trials delivered conflicting results and PDE5 inhibitor treatment failed to show a beneficial effect in patients [Leung D G et al., *Ann Neurol.* 2014 October; 76(4):541-9; Victor R G et al., *Neurology.* 2017 Oct. 24; 89(17):1811-1820] despite promising preclinical results including preclinical models in which sGC stimulators were used (WO 2015/106268 A1). This could be due to the fact that PDE5 inhibitors and sGC stimulators might be only effective when sufficient NO/cGMP is produced (PDE5i) and when sufficient heme-containing sGC is expressed. Both sufficient endogenous cGMP production and expression of heme-containing sGC might be impaired in muscular dystrophies. In addition, dysregulation of the NO/cGMP/PDE axis might only be in part responsible for the development and progression of muscular dystrophies. Other pathways could also significantly contribute to the disease phenotype and diseases severity of muscular dystrophies. More recently, Ironwood Pharmaceuticals claimed the use of sGC stimulators for treatment of DMD (WO 2015/106268 A1) and Johns Hopkins claimed the use of sGC activators for the treatment of DMD (WO 2014/190250 A1).

Aldosterone plays a key part in maintaining fluid and electrolyte homeostasis by promoting, in the epithelium of the distal nephron, sodium retention and potassium secretion, thus contributing to keeping the extracellular volume constant and thus to regulating blood pressure. Besides this, aldosterone displays direct effects on the structure and function of the cardiac and vascular system, but the underlying mechanisms thereof are not yet fully explained [R E. Booth, J. P. Johnson, J. D. Stockand, *Adv. Physiol. Educ.* 26 (1), 8-20 (2002)].

Aldosterone is a steroid hormone which is formed in the adrenal cortex. Its production is regulated indirectly very substantially depending on the renal blood flow. Any decrease in renal blood flow leads to release in the kidney of the enzyme renin into the circulating blood. This in turn activates the formation of angiotensin II, which on the one hand has a constricting effect on the arterial blood vessels, but on the other hand also stimulates the formation of aldosterone in the adrenal cortex. Thus, the kidney acts as blood pressure sensor, and thus indirect volume sensor in the circulating blood and counteracts via the renin-angiotensin-aldosterone system critical losses of volume by on the one hand increasing the blood pressure (angiotensin II effect), and on the other hand by rebalancing the state of filling of the vascular system by increased reabsorption of sodium and water in the kidney (aldosterone effect).

This control system may be pathologically impaired in diverse ways. Thus, a chronic reduction in renal blood flow (e.g. as a result of heart failure and the congestion of blood in the venous system caused thereby) leads to a chronically excessive release of aldosterone. In turn this is followed by an expansion of the blood volume and thereby increases the weakness of the heart through an excessive supply of volume to the heart. Congestion of blood in the lungs with shortness of breath and formation of edema in the extremities, and ascites and pleural effusions may be the result; the renal blood flow falls further. In addition, the excessive aldosterone effect leads to a reduction in the potassium concentration in the blood and in the extracellular fluid. In heart muscles which have been previously damaged otherwise, cardiac arrhythmias with a fatal outcome may be induced if there is a deviation below a critical minimum level. This is likely to be one of the main causes of the sudden cardiac death which frequently occurs in patients with heart failure.

In addition, aldosterone is also thought to be responsible for a number of the myocardial remodeling processes typically to be observed in heart failure. Thus, hyperaldosteronism is a crucial component in the pathogenesis and prognosis of heart failure which may originally be induced by various types of damage such as, for example, a myocardial infarction, a myocardial inflammation or high blood pressure. This assumption is supported by the fact that there was a marked reduction in overall mortality in wide-ranging clinical studies on groups of patients with chronic heart failure and post-myocardial infarction through the use of MRAs [B. Pitt, F. Zannad, W. J. Remme et al., *N. Engl. J. Med.* 341, 709-717 (1999); B. Pitt, W. Remme, F. Zannad et al., *N. Engl. J. Med.* 348, 1309-1321 (2003)]. It was possible to achieve this inter alia by reducing the incidence of sudden cardiac death.

The effects of aldosterone are mediated by the mineralocorticoid receptor which has an intracellular location in the target cells. MRAs available to date, have, like aldosterone itself, a basic steroid structure. The utility of such steroidal antagonists is limited by their interactions with the receptors of other steroid hormones, which in some cases lead to considerable side effects such as gynecomastia and impotence and to discontinuation of the therapy [M. A. Zaman, S. Oparil, D. A. Calhoun, *Nature Rev. Drug Disc.* 1, 621-636 (2002)].

The use of potent, non-steroidal MRAs which are more selective for the mineralocorticoid receptor provides the possibility of avoiding this profile of side effects and thus achieving a distinct therapeutic advantage. Moreover, in comparison to the available steroidal MRAs, a non-steroidal structure has at least two important consequences for pharmacological downstream effects:

1.) In contrast to the steroidal MRAs spironolactone and eplerenone, the non-steroidal MRA finerenone is a 'bulky' antagonist (Barfacker et al. 2012). Binding of a 'bulky' non-steroidal MRA probably causes a protrusion of helix 12 in MR's C-terminal-activating function 2 domain, and as a consequence a differential recruitment of transcriptional co-factors in comparison to steroidal MRAs (Amazit et al. J Biol Chem. 2015; 290(36):21876-89, Grune et al. J Cardiovasc Pharmacol. 2016; 67(5):402-11; Grune et al. Hypertension. 2018; 71(4):599-608). This specific co-factor recruitment then can lead to a differential gene expression profile in comparison to steroidal MRAs (Grune et al. J Cardiovasc Pharmacol. 2016; 67(5):402-11; Grune et al. Hypertension. 2018; 71(4):599-608).

2.) A non-steroidal chemical structure does not only influence the binding mode within MR, but especially determines the physicochemical properties like lipophilicity and polarity, which have a strong impact on plasma protein binding, transport, tissue penetration and distribution. As an example, the steroidal MRAs are 6- to 10-fold more lipophilic than non-steroidal MRA finerenone, whereas the latter exhibits higher polarity than the steroidal MRAs (Kolkhof et al. Curr Opin Nephrol Hypertens. 2015; 24(5):417-24.). Quantitative wholebody autoradiography with [14C]-labeled finerenone demonstrated a balanced distribution of finerenone into cardiac and kidney tissues of rats, which is in clear contrast to the respective distribution pattern of spironolactone and eplerenone in rodents (Kolkhof et al. J Cardiovasc Pharmacol. 2014; 64(1):69-78.). Taken together, structurally different MRAs can lead to a different pharmacology.

Preclinical studies using dystrophin-deficient mice showed that the Angiotensin Conversion Enzyme (ACE) inhibitor lisinopril given in addition to the steroidal MRA spironolactone from 4 to 20 weeks of age is effective in preventing ongoing skeletal muscle damage and significantly improved muscle force generation in both respiratory and limb muscles (Rafael-Fortney et al. *Circulation*. 2011; 124(5):582-588; Lowe et al., *J Neuromuscul Dis*. 2016; 3(3): 395-404). Moreover, a randomised, double-blind, placebo-controlled trial in DMD boys demonstrated that addition of the steroidal MRA eplerenone to background ACE inhibitor or Angiotensin Receptor Blocker (ARB) therapy attenuates the progressive decline in left ventricular systolic function as determined by LV circumferential strain (a measure of contractile dysfunction) at 12 months [Raman et al., Lancet Neurology 2015 February; 14(2):153-61].

Accordingly, it is an object of the present invention to provide suitable compounds and compound combinations for use in the treatment and/or prevention of a muscular or neuromuscular disease. Moreover, in order to reduce potential medication burden to pediatric DMD patients, a replacement of two medications such as ACE inhibitor or ARB plus spironolactone or eplerenone (steroidal MRAs) by a single compound is desired.

It was found that non-steroidal MRA monotherapy provides similar structural and functional improvements as observed before with a combination therapy of an ACE inhibitor plus the steroidal MRA spironolactone and can be used for the treatment and/or prevention of a muscular or neuromuscular disease preferably in the treatment and/or prevention of pediatric population diagnosed with DMD. Especially preferred in the delay of progression of pediatric population diagnosed with DMD. It was found that non-steroidal mineralocorticoid receptor antagonists in combination with sGC stimulators and/or sGC activators act in a synergistic manner for the treatment and/or prevention of a muscular or neuromuscular disease, such as but not limited to the improvement of muscular functions, e.g. of hearts, striated and non-striated muscles.

According to the current invention the results for Finerenone monotherapie support the use of Finerenone especially for pediatric DMD patients as the burden of medication can be reduced to one single compound.

Definitions

The term "muscular or neuromuscular disease" refers to a medical condition that affects the muscles and/or their direct nervous system control. They can be acquired or of genetic origin. In particular, muscular or neuromuscular diseases are characterized for example by Duchenne muscular dystrophy (DMD), Becker muscular dystrophy (BMD), Congenital muscular dystrophy, Miyoshi myopathy, Emery-Dreifuss muscular dystrophy, Facioscapulohumeral muscular dystrophy, Limb-girdle muscular dystrophy, Myotonic muscular dystrophy, Oculopharyngeal muscular dystrophy, Myasthenia gravis, Lambert-Eaton myasthenic syndrome and Charcot-Marie-Tooth disease.

Typical symptoms of most forms of muscular or neuromuscular diseases include progressive muscular wasting, poor balance, drooping eyelids, atrophy, scoliosis (curvature of the spine and the back), inability to walk, frequent falls, waddling gait, calf deformation, limited range of movement, respiratory difficulty, joint contractures, cardiomyopathy, arrhythmias and muscle spasms.

The main symptom of Duchenne Muscular Dystrophy (DMD) is muscle weakness associated with muscle wasting with the voluntary muscles being first affected, especially the muscles of the hips, pelvic area, thighs, shoulders, and calf muscles. Muscle weakness also occurs in the arms, neck, and other areas, but not as early as in the lower half of the body. Calves are often enlarged. Symptoms usually appear before age 6 and may appear as early as infancy. Problems with muscles in the upper part of the body (e.g., intercostals and diaphragm) are generally manifested as respiratory difficulties. Other physical symptoms of DMD include but are not limited to: awkward manner of walking, stepping, or running (patients tend to walk on their forefeet, because of an increased calf tonus; toe walking is a compensatory adaptation to knee extensor weakness); frequent falls; fatigue; difficulty with motor skills (e.g., running, hopping and jumping); increased lumbar lordosis, leading to shortening of the hip-flexor muscles which has an effect on overall posture and the manner of walking, stepping, or running; muscle contractures of Achilles tendon and hamstrings; impaired functionality because the muscle fibers shorten and fibrosis occurs in connective tissue; progressive difficulty walking; muscle fiber deformities; pseudohypertrophy or enlarging of tongue and calf muscles (calf enlargement often happens during the ages of 5 to 15, and the muscle tissue is eventually replaced by fat and connective tissue as the legs become less used, hence the term pseudohypertrophy); use of Gower's maneuver to raise from the floor; higher risk of neurobehavioral disorders (e.g., ADHD), learning disorders (dyslexia), and non-progressive weaknesses in specific cognitive skills (in particular short-term verbal memory), which are believed to be the result of absent or dysfunctional dystrophin in the brain; eventual loss of ability to walk (usually by the age of 12); skeletal deformities (including scoliosis); and cardiomyopathy.

Within the meaning of the present invention, the terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

Within the meaning of the present invention, the terms "treat", "treating" or "treatment" with regard to a disorder or disease refers to alleviating or abrogating the cause and/or effects or symptoms of the disorder or disease. As used herein, the terms "treat", "treatment" and "treating" refer to the reduction or amelioration or slowing down of the progression, severity and/or duration of a muscular and/or neuromuscular disease (e.g., a Muscular Dystrophy), or the reduction, amelioration or slowing down of the progression, the severity and/or the duration of one or more symptoms (preferably, one or more measurable symptoms) of the condition, as a result of the administration of one or more therapies (e.g., at least one non-steroidal MRA or a pharmaceutically acceptable salt thereof, either alone or in combination with at least one sGC Stimulator. In some embodiments, the terms "treat," "treatment" and "treating" refer to delaying the onset of a symptom or set of symptoms or to delaying the onset of a loss in certain physical function (e.g., muscular function, walking). In some embodiments, the terms "treat," "treatment" and "treating" refer to the amelioration of at least one measurable physical parameter of a muscular and/or neuromuscular disease (e.g., a Muscular Dystrophy). In other embodiments the terms "treat", "treatment" and "treating" refer to the reduction, inhibition or slowing down of the progression of said condition, either physically by, e.g., stabilization of a measurable symptom (e.g., fatigue), or physiologically by, e.g., stabilization of a measurable parameter (e.g., skeletal Troponin I levels), or both. As used herein, the term "treating", "treat" or "treatment" also refer to averting the cause and/or effects of a disease or disorder or one of the symptoms developed as a result of the disease or disorder prior to the disease or disorder fully manifesting itself. The treatment or prevention of a disease, a condition, a disorder, an injury or a health problem may be partial or complete.

Within the meaning of the present invention, the term "sGC activator" refers to molecules that are able to activate heme-free apo sGC. They are defined as NO-independent and heme-independent sGC activators. Common characteristics of these substances are that in combination with NO they only have an additive effect on enzyme activation, and that the activation of the oxidized or heme-free enzyme is markedly higher than that of the heme-containing enzyme (Evgenov et al. 2006; Stasch J P et al. 2002; Stasch J P et al. 2006).

Within the meaning of the present invention, the term "non-steroidal mineralocorticoid receptor antagonist" refers to synthetic, small molecular mineralocorticoid receptor antagonists that are not based on a steroidal, more specifically a sterane or partially unsaturated sterane, chemical structure.

EMBODIMENTS

One embodiment of the invention is a non-steroidal MR Antagonist or a pharmaceutically acceptable salt thereof for use in the treatment and/or prevention of a muscular or neuromuscular disease.

According to a further embodiment, the invention provides non-steroidal MR Antagonists for use in the treatment and/or prevention of a muscular or neuromuscular disease, wherein the non-steroidal mineralocorticoid receptor antagonist is selected from the group consisting of (4S)-4-(4-cyano-2-methoxyphenyl)-5-ethoxy-2,8-dimethyl-1,4-dihydro-1,6-naphthyridine-3-carboxamide, 1-(2-hydroxyethyl)-4-methyl-N-(4-(methylsulfonyl)phenyl)-5-(2-(trifluoromethyl) phenyl)-1H-pyrrole-3-carboxamide, N-(4-(4-fluorophenyl)-2,2-dimethyl-3-oxo-3,4-dihydro-2H-benzo[b][1,4]oxazin-7-yl)methanesulfonamide, (3S,3aR)-2-(3-Chloro-4-cyanophenyl)-3-cyclopentyl-3,3a,4,5-tetrahydro-2H-benzo[g]indazole-7-carboxylic acid, (R)-6-(1-(4-cyano-3-methylphenyl)-5-cyclopentyl-4,5-dihydro-1H-pyrazol-3-yl)-2-methoxynicotinic acid,

KBP-5074, 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile, (S)—N-{3-[1-cyclopropyl-1-(2,4-difluoro-phenyl)-ethyl]-1H-indol-7-yl}-methanesulfonamide,

SM-368229,

LY2623091,

LY3045697,

MT-3995,

CS-3150 and

AZD9977 or a pharmaceutically acceptable salt thereof.

In another preferred embodiment the non-steroidal MR Antagonist for use in the treatment and/or prevention of a muscular or neuromuscular disease is Finerenone (S)-4-(4-Cyano-2-methoxyphenyl)-5-ethoxy-2,8-dimethyl-1,4-dihydro-1,6-naphthyridin-3-carboxamid) according to formula (I)

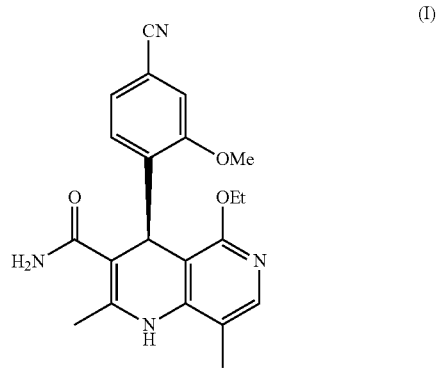 [SMILES: CCOc1ncc(C)c2c1[C@H](c1ccc(C#N)cc1OC)C(C(N)=O)=C(C)N2]

or a pharmaceutically acceptable salt thereof.

One embodiment of the invention is at least one non-steroidal MR Antagonist or a pharmaceutically acceptable salt thereof, and at least one more additional therapeutic agent, for use in the treatment of a muscular or neuromuscular disease.

One embodiment of the invention is a pharmaceutical composition comprising at least one non-steroidal MR Antagonist or a pharmaceutically acceptable salt thereof, and at least one more additional therapeutic agent, for use in the treatment of a muscular or neuromuscular disease.

One embodiment of the invention is at least one non-steroidal MR Antagonist or a pharmaceutically acceptable salt thereof in combination with at least one sGC Stimulator for use in the treatment and/or prevention of a muscular or neuromuscular disease.

One embodiment of the invention is at least one non-steroidal MR Antagonist or a pharmaceutically acceptable salt thereof in combination with at least one sGC activator for use in the treatment and/or prevention of a muscular or neuromuscular disease.

One embodiment of the invention is a pharmaceutical composition comprising at least one non-steroidal MR Antagonist or a pharmaceutically acceptable salt thereof in combination with at least one sGC Stimulator for use in the treatment and/or prevention of a muscular or neuromuscular disease.

One embodiment of the invention is a pharmaceutical composition comprising at least one non-steroidal MR Antagonist or a pharmaceutically acceptable salt thereof in combination with at least one sGC activator for use in the treatment and/or prevention of a muscular or neuromuscular disease.

One embodiment of the invention is a pharmaceutical composition comprising at least one non-steroidal MR Antagonist in combination with at least one sGC stimulator for use in the treatment and/or prevention of a muscular or neuromuscular disease, wherein the at least one non-steroidal MR Antagonist is (S)-4-(4-Cyano-2-methoxyphenyl)-5-ethoxy-2,8-dimethyl-1,4-dihydro-1,6-naphthyridin-3-carboxamid according to formula (I)

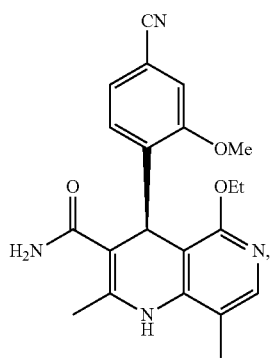 (I)

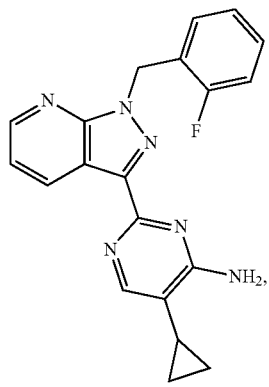 (II)

or a pharmaceutically acceptable salt thereof and wherein the at least one sGC stimulator is selected from the group consisting of:
2-[1-(2-fluorobenzyl)-1H-pyrazolo[3,4-b]pyridin-3-yl]-5-(4-morpholinyl)-4,6-pyrimidinediamine,
2-[1-(2-fluorobenzyl)-1H-pyrazolo[3,4-b]pyridin-3-yl]-5-(4-pyridinyl)-4-pyrimidineamine,
methyl {4,6-diamino-2-[5-fluoro-1-(2-fluorobenzyl)-1H-pyrazolo[3,4-b]pyridine-3-yl]pyrimidin-5-yl}carbamate (Vericiguat, compound of formula (III), known from WO 2011/147809, example 1),
methyl {4,6-diamino-2-[5-fluoro-1-(2-fluorobenzyl)-1H-pyrazolo[3,4-b]pyridine-3-yl]pyrimidin-5-yl}methylcarbamate,
methyl {4,6-diamino-2-[5-fluoro-1-(2-fluorobenzyl)-1H-pyrazolo[3,4-b]pyridin-3-yl]pyrimidin-5-yl}(2,2,2-trifluoroethyl)carbamate,
4-amino-2-[5-chloro-3(3,3,3-trifluoropropyl)-1H-indazol-1-yl]-5,5-dimethyl-5,7-dihydro-6H-pyrrolo[2,3-d]pyrimidin-6-one,
4-amino-2[5-chloro-3-(2,3,6-trifluorobenzyl)-1H-indazol-1-yl]-5,5-dimethyl-5,7-dihydro-6H-pyrrolo[2,3-d]pyrimidin-6-one,
4-amino-5,5-dimethyl-2-[3-(2,3,6-trifluorobenzyl)1H-thieno[3,4-c]pyrazol-1-yl]-5,7-dihydro-6H-pyrrolo[2,3-d]pyrimidin-6-one,
4-amino-5,5-dimethyl-2-[3-(2,3,6-trifluorobenzyl)-1H-thieno[2,3-d]pyrazol-1-yl]-5,5-dimethyl-5,7-dihydro-6H-pyrrolo[2,3-d]pyrimidin-6-one,
4-amino-5,5-dimethyl-2-[7-(2,3,6-trifluorobenzyl)imidazo[1,5-b]pyridazin-5-yl]-5,7-dihydro-6H-pyrrolo[2,3-d]pyrimidin-6-one,
4-amino-2-[6-chloro-3-(2,3,6-trifluorobenzyl)imidazo[1,5-a]pyridin-1-yl]]-5,5-dimethyl-5,7-dihydro-6H-pyrrolo[2,3-d]pyrimidin-6-one,
4-amino-2-[6-fluoro-3-(2,3,6-trifluorobenzyl)imidazo[1,5-a]pyridin-1-yl]]-5,5-dimethyl-5,7-dihydro-6H-pyrrolo[2,3-d]pyrimidin-6-one,
4-amino-2-[6-fluoro-3-(2,3,6-trifluorobenzyl)6-fluoroimidazo[1,5-a]pyridin-1-yl]-5,5-dimethyl-5,7-dihydro-6H-pyrrolo[2,3-d]pyrimidin-6-one,
4-amino-5,5-dimethyl-2-[3-(2,4,6-trifluorobenzyl)imidazo[1,5-a]pyridin-1-yl]]-5,7-dihydro-6H-pyrrolo[2,3-d]pyrimidin-6-one,
4-amino-2-[3-(2-cyclopentylethyl)imidazo[1,5-a]pyridin-1-yl]-5,5-dimethyl-5,7-dihydro-6H-pyrrolo[2,3-d]pyrimidin-6-one,
3-(4-amino-5-cyclopropylpyrimidin-2-yl)-1-(2-fluorobenzyl)-1H-pyrazolo[3,4-b]pyridine (BAY 41-2272, compound of formula (II)), 2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one,
ent-N-[(2S)-amino-2-methylbutyl]-8-[(2,6-difluorobenzyl)oxy]-2,6-dimethylimidazo[1,2-a]pyridine-3-carboxamide (enantiomer A, compound of formula (IV)), known from WO 2014/068099, example 200),
ent-N-(2-amino-2-methylbutyl)-8-[(2,6-difluorobenzyl)oxy]-2,6-dimethylimidazo[1,2-a]pyridine-3-carboxamide (enantiomer B),
ent-N-(2-amino-5,5,5-trifluoro-2-methylpentyl)-2,6-dimethyl-8-[(2,3,6-trifluorobenzyl)oxy]imidazo[1,2-a]pyridine-3-carboxamide (enantiomer B),
ent-N-(2-amino-5,5,5-trifluoro-2-methylpentyl)-8-[(2,6-difluorobenzyl)oxy]-2,6-dimethylimidazo[1,2-a]pyridine-3-carboxamide (enantiomer B),
ent-N-(2-amino-5,5,5-trifluoro-2-methylpentyl)-8-[(2,6-difluorobenzyl)oxy]-2,6-dimethylimidazo[1,2-a]pyridine-3-carboxamide (enantiomer A),
ent-N-(2-amino-3-fluoro-2-methylpropyl)-2,6-dimethyl-8-[(2,3,6-trifluorobenzyl)oxy]imidazo[1,2-a]pyridine-3-carboxamide (enantiomer B),
ent-N-(2-amino-3-fluoro-2-methylpropyl)-8-[(2,6-difluorobenzyl)oxy]-2,6-dimethylimidazo[1,2-a]pyridine-3-carboxamide (enantiomer B),
ent-N-(2-amino-3-fluoro-2-methylpropyl)-8-[(2,6-difluorobenzyl)oxy]-2,6-dimethylimidazo[1,2-a]pyridine-3-carboxamide (enantiomer A),
rac-N-(2-amino-3-fluoro-2-methylpropyl)-8-[(2,6-difluorobenzyl)oxy]-2,6-dimethylimidazo[1,2-a]pyridine-3-carboxamide formate,
ent-N-(2-amino-3-fluoro-2-methylpropyl)-2,6-dimethyl-8-[(2,3,6-trifluorobenzyl)oxy]imidazo[1,2-a]pyridine-3-carboxamide (enantiomer A),
ent-N-(2-amino-3-fluoro-2-methylpropyl)-8-[(2,6-difluorobenzyl)oxy]-6-(difluoromethyl)-2-methylimidazo[1,2-a]pyridine-3-carboxamide (enantiomer B),
ent-N-(2-amino-3-fluoro-2-methylpropyl)-8-[(2,6-difluorobenzyl)oxy]-6-(difluoromethyl)-2-methylimidazo[1,2-a]pyridine-3-carboxamide (enantiomer A),
ent-N-(2-amino-3-fluoro-2-methylpropyl)-8-[(2,6-difluorobenzyl)oxy]-6-(fluoromethyl)-2-methylimidazo[1,2-a]pyridine-3-carboxamide,
1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat),
5-fluoro-2-[1-(2-fluorobenzyl)-5-(1,2-oxazol-3-yl)-1H-pyrazol-3-yl]pyrimidin-4-ol (IWP-051), IWP-121, IWP-427, IWP-953, IW-1701 and IW-6463, or a pharmaceutically acceptable salt thereof.

According to a further embodiment of the present invention, sGC stimulators for use according to the invention are selected from the group consisting of:
2-[1-(2-fluorobenzyl)-1H-pyrazolo[3,4-b]pyridin-3-yl]-5-(4-morpholinyl)-4,6-pyrimidinediamine,
2-[1-(2-fluorobenzyl)-1H-pyrazolo[3,4-b]pyridin-3-yl]-5-(4-pyridinyl)-4-pyrimidineamine
methyl {4,6-diamino-2-[5-fluoro-1-(2-fluorobenzyl)-1H-pyrazolo[3,4-b]pyridine-3-yl]pyrimidin-5-yl}carbamate (Vericiguat, compound of formula (III)),
ent-N-[(2S)-amino-2-methylbutyl]-8-[(2,6-difluorobenzyl)oxy]-2,6-dimethylimidazo[1,2-a]pyridine-3-carboxamide (enantiomer A, compound of formula (IV)),
ent-N-(2-amino-2-methylbutyl)-8-[(2,6-difluorobenzyl)oxy]-2,6-dimethylimidazo[1,2-a]pyridine-3-carboxamide (enantiomer B),
methyl {4,6-diamino-2-[5-fluoro-1-(2-fluorobenzyl)-1H-pyrazolo[3,4-b]pyridine-3-yl]pyrimidin-5-yl}methylcarbamate,
methyl {4,6-diamino-2-[5-fluoro-1-(2-fluorobenzyl)-1H-pyrazolo[3,4-b]pyridin-3-yl]pyrimidin-5-yl}(2,2,2-trifluoroethyl)carbamate,
4-amino-2-[5-chloro-3(3,3,3-trifluoropropyl)-1H-indazol-1-yl]-5,5-dimethyl-5,7-dihydro-6H-pyrrolo[2,3-d]pyrimidin-6-one,
4-amino-2[5-chloro-3-(2,3,6-trifluorobenzyl)-1H-indazol-1-yl]-5,5-dimethyl-5,7-dihydro-6H-pyrrolo[2,3-d]pyrimidin-6-one,
4-amino-5,5-dimethyl-2-[3-(2,3,6-trifluorobenzyl)1H-thieno[3,4-c]pyrazol-1-yl]-5,7-dihydro-6H-pyrrolo[2,3-d]pyrimidin-6-one,
4-amino-5,5-dimethyl-2-[3-(2,3,6-trifluorobenzyl)-1H-thieno[2,3-d]pyrazol-1-yl]-5,5-dimethyl-5,7-dihydro-6H-pyrrolo[2,3-d]pyrimidin-6-one,
4-amino-5,5-dimethyl-2-[7-(2,3,6-trifluorobenzyl)imidazo[1,5-b]pyridazin-5-yl]-5,7-dihydro-6H-pyrrolo[2,3-d]pyrimidin-6-one,
4-amino-2-[6-chloro-3-(2,3,6-trifluorobenzyl)imidazo[1,5-a]pyridin-1-yl]]-5,5-dimethyl-5,7-dihydro-6H-pyrrolo[2,3-d]pyrimidin-6-one,
4-amino-2-[6-fluoro-3-(2,3,6-trifluorobenzyl)imidazo[1,5-a]pyridin-1-yl]]-5,5-dimethyl-5,7-dihydro-6H-pyrrolo[2,3-d]pyrimidin-6-one,
4-amino-2-[6-fluoro-3-(2,3,6-trifluorobenzyl)6-fluoroimidazo[1,5-a]pyridin-1-yl]-5,5-dimethyl-5,7-dihydro-6H-pyrrolo[2,3-d]pyrimidin-6-one,
4-amino-5,5-dimethyl-2-[3-(2,4,6-trifluorobenzyl)imidazo[1,5-a]pyridin-1-yl]]-5,7-dihydro-6H-pyrrolo[2,3-d]pyrimidin-6-one,
4-amino-2-[3-(2-cyclopentylethyl)imidazo[1,5-a]pyridin-1-yl]-5,5-dimethyl-5,7-dihydro-6H-pyrrolo[2,3-d]pyrimidin-6-one,
3-(4-amino-5-cyclopropylpyrimidin-2-yl)-1-(2-fluorobenzyl)-1H-pyrazolo[3,4-b]pyridine,
2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one and
1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat), or a pharmaceutically acceptable salt thereof.

According to a further embodiment of the present invention, sGC stimulators for use according to the invention are selected from the group consisting of:
2-[1-(2-fluorobenzyl)-1H-pyrazolo[3,4-b]pyridin-3-yl]-5-(4-morpholinyl)-4,6-pyrimidinediamine,
2-[1-(2-fluorobenzyl)-1H-pyrazolo[3,4-b]pyridin-3-yl]-5-(4-pyridinyl)-4-pyrimidineamine
methyl {4,6-diamino-2-[5-fluoro-1-(2-fluorobenzyl)-1H-pyrazolo[3,4-b]pyridine-3-yl]pyrimidin-5-yl}carbamate (Vericiguat, compound of formula (III)),
ent-N-[(2S)-amino-2-methylbutyl]-8-[(2,6-difluorobenzyl)oxy]-2,6-dimethylimidazo[1,2-a]pyridine-3-carboxamide (enantiomer A, compound of formula (IV)),
ent-N-(2-amino-2-methylbutyl)-8-[(2,6-difluorobenzyl)oxy]-2,6-dimethylimidazo[1,2-a]pyridine-3-carboxamide (enantiomer B),
methyl {4,6-diamino-2-[5-fluoro-1-(2-fluorobenzyl)-1H-pyrazolo[3,4-b]pyridine-3-yl]pyrimidin-5-yl}methylcarbamate,
3-(4-amino-5-cyclopropylpyrimidin-2-yl)-1-(2-fluorobenzyl)-1H-pyrazolo[3,4-b]pyridine,
2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one and
1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat), or a pharmaceutically acceptable salt thereof.

According to a further embodiment of the present invention, sGC stimulators for use according to the invention are selected from the group consisting of:
methyl {4,6-diamino-2-[5-fluoro-1-(2-fluorobenzyl)-1H-pyrazolo[3,4-b]pyridine-3-yl]pyrimidin-5-yl}carbamate (Vericiguat, compound of formula (III)),
ent-N-[(2S)-amino-2-methylbutyl]-8-[(2,6-difluorobenzyl)oxy]-2,6-dimethylimidazo[1,2-a]pyridine-3-carboxamide (enantiomer A, compound of formula (IV)),
ent-N-(2-amino-2-methylbutyl)-8-[(2,6-difluorobenzyl)oxy]-2,6-dimethylimidazo[1,2-a]pyridine-3-carboxamide (enantiomer B),
methyl {4,6-diamino-2-[5-fluoro-1-(2-fluorobenzyl)-1H-pyrazolo[3,4-b]pyridine-3-yl]pyrimidin-5-yl}methylcarbamate,
2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one and
1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat), or a pharmaceutically acceptable salt thereof.

According to a further embodiment of the present invention, sGC stimulators for use according to the invention are selected from the group consisting of:
methyl {4,6-diamino-2-[5-fluoro-1-(2-fluorobenzyl)-1H-pyrazolo[3,4-b]pyridine-3-yl]pyrimidin-5-yl}carbamate (Vericiguat, compound of formula (III)),
ent-N-[(2S)-amino-2-methylbutyl]-8-[(2,6-difluorobenzyl)oxy]-2,6-dimethylimidazo[1,2-a]pyridine-3-carboxamide (enantiomer A, compound of formula (IV)),
ent-N-(2-amino-2-methylbutyl)-8-[(2,6-difluorobenzyl)oxy]-2,6-dimethylimidazo[1,2-a]pyridine-3-carboxamide (enantiomer B),
1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat) and
3-(4-amino-5-cyclopropylpyrimidin-2-yl)-1-(2-fluorobenzyl)-1H-pyrazolo[3,4-b]pyridine (BAY 41-2272, compound of formula (II))
or a pharmaceutically acceptable salt thereof.

According to a further embodiment of the present invention, sGC stimulators for use according to the invention are selected from the group consisting of:
methyl 4,6-diamino-2-[1-(2-fluorobenzyl)-1H-pyrazolo[3,4-b]pyridin-3-yl]-5-pyrimidinyl(methyl)carbamate (Riociguat),
methyl {4,6-diamino-2-[5-fluoro-1-(2-fluorobenzyl)-1H-pyrazolo[3,4-b]pyridine-3-yl]pyrimidin-5-yl}carbamate (Vericiguat),
3-(4-amino-5-cyclopropylpyrimidin-2-yl)-1-(2-fluorobenzyl)-1H-pyrazolo[3,4-b]pyridine (BAY 41-2272) and
1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat)
or a pharmaceutically acceptable salt thereof.

According to a further embodiment of the present invention, the sGC stimulators for use according to the invention is 3-(4-amino-5-cyclopropylpyrimidin-2-yl)-1-(2-fluorobenzyl)-1H-pyrazolo[3,4-b]pyridine (BAY 41-2272) or a pharmaceutically acceptable salt thereof.

A further embodiment of the invention is at least one sGC stimulator selected from the group consisting of
methyl {4,6-diamino-2-[5-fluoro-1-(2-fluorobenzyl)-1H-pyrazolo[3,4-b]pyridine-3-yl]pyrimidin-5-yl}carbamate (Vericiguat, compound of formula (III)),
ent-N-[(2S)-amino-2-methylbutyl]-8-[(2,6-difluorobenzyl)oxy]-2,6-dimethylimidazo[1,2-a]pyridine-3-carboxamide (enantiomer A, compound of formula (IV)),
ent-N-(2-amino-2-methylbutyl)-8-[(2,6-difluorobenzyl)oxy]-2,6-dimethylimidazo[1,2-a]pyridine-3-carboxamide (enantiomer B),
1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat) and
3-(4-amino-5-cyclopropylpyrimidin-2-yl)-1-(2-fluorobenzyl)-1H-pyrazolo[3,4-b]pyridine (BAY 41-2272, compound of formula (II))
or a pharmaceutically acceptable salt thereof
in combination with at least one non-steroidal mineralocorticoid receptor antagonist selected from the group consisting of
(4S)-4-(4-cyano-2-methoxyphenyl)-5-ethoxy-2,8-dimethyl-1,4-dihydro-1,6-naphthyridine-3-carboxamide,
1-(2-hydroxyethyl)-4-methyl-N-(4-(methylsulfonyl)phenyl)-5-(2-(trifluoromethyl) phenyl)-1H-pyrrole-3-carboxamide,
N-(4-(4-fluorophenyl)-2,2-dimethyl-3-oxo-3,4-dihydro-2H-benzo[b][1,4]oxazin-7-yl)methanesulfonamide,
(3S,3aR)-2-(3-Chloro-4-cyanophenyl)-3-cyclopentyl-3,3a,4,5-tetrahydro-2H-benzo[g]indazole-7-carboxylic acid,
(R)-6-(1-(4-cyano-3-methylphenyl)-5-cyclopentyl-4,5-dihydro-1H-pyrazol-3-yl)-2-methoxynicotinic acid,
KBP-5074,
2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile,
(S)—N-{3-[1-cyclopropyl-1-(2,4-difluoro-phenyl)-ethyl]-1H-indol-7-yl}-methanesulfonamide,
SM-368229,
LY2623091,
LY3045697,
MT-3995,
CS-3150 and
AZD9977 or a pharmaceutically acceptable salt thereof for use in the treatment and/or prevention of a muscular or neuromuscular disease.

According to a further embodiment of the present invention, the sGC stimulator for use according to the invention is:
methyl {4,6-diamino-2-[5-fluoro-1-(2-fluorobenzyl)-1H-pyrazolo[3,4-b]pyridine-3-yl]pyrimidin-5-yl}carbamate (Vericiguat, compound of formula (III))

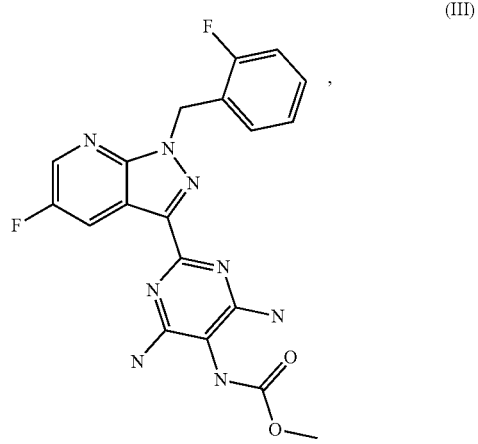 [SMILES: COC(=O)Nc1c(N)nc(-c2nn(Cc3ccccc3F)c3ncc(F)cc23)nc1N]

or a pharmaceutically acceptable salt thereof.

According to a further embodiment of the present invention, the sGC stimulator for use according to the invention is:
ent-N-[(2S)-amino-2-methylbutyl]-8-[(2,6-difluorobenzyl)oxy]-2,6-dimethylimidazo[1,2-a]pyridine-3-carboxamide (enantiomer A) (compound of formula (IV))

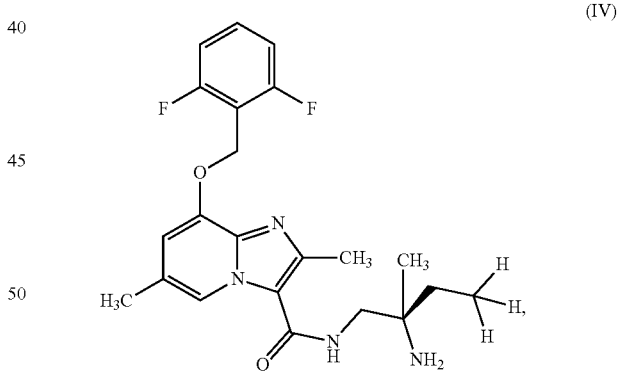

or a pharmaceutically acceptable salt thereof.

One embodiment of the invention is at least one non-steroidal MR Antagonist in combination with at least one sGC activator for use in the treatment and/or prevention of a muscular or neuromuscular disease.

One embodiment of the invention is a pharmaceutical composition comprising at least one non-steroidal MR Antagonist in combination with at least one sGC activator for use in the treatment and/or prevention of a muscular or neuromuscular disease.

One embodiment of the invention is a pharmaceutical composition comprising at least one non-steroidal MR Antagonist in combination with at least one sGC activator for use in the treatment and/or prevention of a muscular or neuromuscular disease, wherein the at least one non-steroidal mineralocorticoid receptor antagonist is (S)-4-(4-Cyano-2-methoxyphenyl)-5-ethoxy-2,8-dimethyl-1,4-dihydro-1,6-naphthyridin-3-carboxamid according to formula (I)

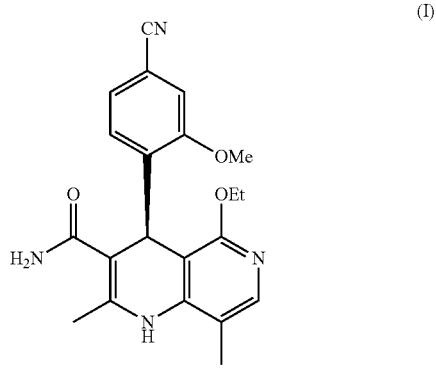 [SMILES: CCOc1ncc(C)c2c1[C@H](c1ccc(C#N)cc1OC)C(C(N)=O)=C(C)N2]

(I)

or a pharmaceutically acceptable salt thereof and wherein the at least on sGC activator is selected from the group consisting of
4-({(4-carboxybutyl) [2-(2-{[4-(2-phenylethyl)benzyl]oxy}phenyl)ethyl]amino}methyl)benzoic acid; (INN: Cinaciguat),
5-chloro-2-(5-chlorothiophene-2-sulfonylamino-N-(4-(morpholine-4-sulfonyl)phenyl)benzamide as sodium salt,
2-(4-chlorophenylsulfonylamino)-4,5-dimethoxy-N-(4-(thiomorpholine-4-sulfonyl)phenyl)benzamide,
1-{6-[5-chloro-2-({4-trans-4-}trifluoromethyl)cyclohexyl]benzyl}oxy)phenyl]pyridin-2-yl}-5-(trifluoromethyl)-1H-pyrazole-4-carboxylic acid,
1-[6-(2-(2-methyl-4-(4-trifluoromethoxyphenyl)benzyloxy)phenyl)pyridin-2-yl]-5-trifluoromethylpyrazole-4-carboxylic acid,
1[6-(3,4-dichlorophenyl)-2-pyridinyl-5-(trifluoromethyl)-1H-pyrazole-4-carboxylic acid
1-({2-[3-chloro-5-(trifluoromethyl)phenyl]-5-methyl-1,3-thiazol-4-yl}methyl)-1H-pyrazole-4-carboxylic acid,
4-({2-[3-(trifluoromethyl)phenyl]-1,3-thiazol-4-yl}methyl) benzoic acid
1-({2-[2-fluoro-3-(trifluoromethyl)phenyl]-5-methyl-1,3-thiazol-4-yl}methyl)-1H-pyrazole-4-carboxylic acid,
3-(4-chloro-3-{[(2S,3R)-2-(4-chlorophenyl)-4,4,4-trifluoro-3-methylbutanoyl]amino}phenyl)-3-cyclopropylpropanoic acid,
5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid,
5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid,
(1R,5S)-3-[4-(5-methyl-2-{[2-methyl-4-(piperidin-1-ylcarbonyl)benzyl]oxy}phenyl)-1,3-thiazol-2-yl]-3-azabicyclo[3.2.1]octane-8-carboxylic acid,
1-[6-(5-methyl-2-{[2-(tetrahydro-2H-pyran-4-yl)-1,2,3,4-tetrahydroisoquinolin-6-yl]methoxyl}phenyl)pyridin-2-yl]-5-(trifluoromethyl)-1H-pyrazole-4-carboxylic acid,
BI-703704 and
BI-684067
or a pharmaceutically acceptable salt thereof.
A further embodiment of the invention is a pharmaceutical composition comprising at least one non-steroidal MR Antagonist in combination with at least one s GC activator for use in the treatment and/or prevention of a muscular or neuromuscular disease, wherein the at least one non-steroidal mineralocorticoid receptor antagonist is (S)-4-(4-Cyano-2-methoxyphenyl)-5-ethoxy-2,8-dimethyl-1,4-dihydro-1,6-naphthyridin-3-carboxamid according to formula (I)

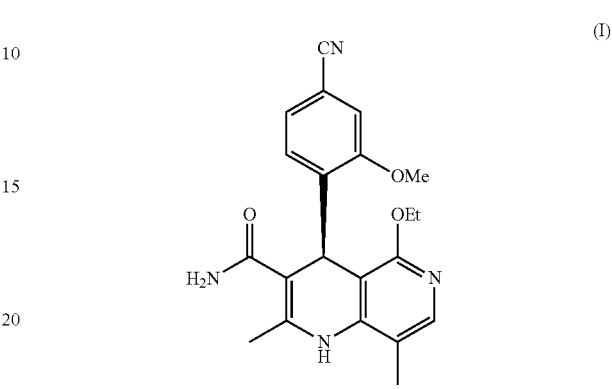

(I)

or a pharmaceutically acceptable salt thereof and wherein the at least on sGC activator is selected from the group consisting of
3-(4-chloro-3-{[(2S,3R)-2-(4-chlorophenyl)-4,4,4-trifluoro-3-methylbutanoyl]amino}phenyl)-3-cyclopropylpropanoic acid,
5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid,
5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid,
or a pharmaceutically acceptable salt thereof.
A further embodiment of the invention is a pharmaceutical composition comprising at least one sGC activator selected from the group consisting of
3-(4-chloro-3-{[(2S,3R)-2-(4-chlorophenyl)-4,4,4-trifluoro-3-methylbutanoyl]amino}phenyl)-3-cyclopropylpropanoic acid,
5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid and
5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid
or a pharmaceutically acceptable salt thereof
in combination with at least one non-steroidal MR Antagonist selected from the group consisting of
(4S)-4-(4-cyano-2-methoxyphenyl)-5-ethoxy-2,8-dimethyl-1,4-dihydro-1,6-naphthyridine-3-carboxamide,
1-(2-hydroxyethyl)-4-methyl-N-(4-(methylsulfonyl)phenyl)-5-(2-(trifluoromethyl) phenyl)-1H-pyrrole-3-carboxamide,
N-(4-(4-fluorophenyl)-2,2-dimethyl-3-oxo-3,4-dihydro-2H-benzo[b][1,4]oxazin-7-yl)methanesulfonamide,
(3S,3aR)-2-(3-Chloro-4-cyanophenyl)-3-cyclopentyl-3,3a,4,5-tetrahydro-2H-benzo[g]indazole-7-carboxylic acid,
(R)-6-(1-(4-cyano-3-methylphenyl)-5-cyclopentyl-4,5-dihydro-1H-pyrazol-3-yl)-2-methoxynicotinic acid,
KBP-5074,
2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile, (S)—N-{3-[1-cyclopropyl-1-(2,4-difluoro-phenyl)-ethyl]-1H-indol-7-yl}-methanesulfonamide,
SM-368229,
LY2623091,
LY3045697,
MT-3995,
CS-3150 and
AZD9977 or a pharmaceutically acceptable salt thereof for use in the treatment and/or prevention of a muscular or neuromuscular disease.

One embodiment of the invention is a pharmaceutical composition comprising at least one sGC activator in combination with at least one non-steroidal MR Antagonist for use in the treatment and/or prevention of a muscular or neuromuscular disease, wherein the at least one sGC activator is 3-(4-chloro-3-{[(2S,3R)-2-(4-chlorophenyl)-4,4,4-trifluoro-3-methylbutanoyl]amino}phenyl)-3-cyclopropyl-propanoic acid or a pharmaceutically acceptable salt thereof and the at least one non-steroidal MR Antagonist is (S)-4-(4-Cyano-2-methoxyphenyl)-5-ethoxy-2,8-dimethyl-1,4-dihydro-1,6-naphthyridin-3-carboxamid according to formula (I) or a pharmaceutically acceptable salt thereof.

One embodiment of the invention is a medicament, comprising a non-steroidal MR Antagonist or a pharmaceutically acceptable salt thereof in combination with one or more inert non-toxic pharmaceutically suitable auxiliaries for use in the treatment and/or prevention of a muscular or neuromuscular disease.

One embodiment of the invention is a medicament, comprising a pharmaceutical composition according to the current invention in combination with one or more inert nontoxic pharmaceutically suitable auxiliaries for use in the treatment and/or prevention of a muscular or neuromuscular disease.

One embodiment of the invention is a method for the treatment and/or prevention of a muscular or neuromuscular disease in humans and animals by administration of an effective amount of at least one non-steroidal MR Antagonist or a pharmaceutically acceptable salt thereof or of a medicament comprising a non-steroidal MR Antagonist or a pharmaceutically acceptable salt thereof in combination with one or more inert non-toxic pharmaceutically suitable auxiliaries.

One embodiment of the invention is a method for the treatment and/or prevention of a muscular or neuromuscular disease in humans and animals by administration of an effective amount of a pharmaceutical composition comprising a non-steroidal MR Antagonist or a pharmaceutically acceptable salt thereof, and at least one more additional therapeutic agent or of a medicament comprising a pharmaceutical composition in combination with one or more inert non-toxic pharmaceutically suitable auxiliaries.

Within the meaning of the aforementioned embodiments the at least one more additional therapeutic agent is preferably a sGC stimulator or a sGC activator as defined above.

Within the meaning of the aforementioned embodiments, the term "muscular or neuromuscular disease" refers to a group of medical conditions consisting of Duchenne muscular dystrophy (DMD), Becker muscular dystrophy (BMD), Congenital muscular dystrophy, Miyoshi myopathy, Emery-Dreifuss muscular dystrophy, Facioscapulohumeral muscular dystrophy, Limb-girdle muscular dystrophy, Myotonic muscular dystrophy, Oculopharyngeal muscular dystrophy, Myasthenia gravis, Lambert-Eaton myasthenic syndrome and Charcot-Marie-Tooth disease.

Within the meaning of the aforementioned embodiments, the term "muscular or neuromuscular disease" preferably is a muscular dystrophy, especially preferred Duchenne muscular dystrophy (DMD).

We identified non-steroidal MRAs for the treatment and/or prevention of muscular or neuromuscular disease.

We identified (S)-4-(4-Cyano-2-methoxyphenyl)-5-ethoxy-2,8-dimethyl-1,4-dihydro-1,6-naphthyridin-3-carboxamid according to formula (I) or a pharmaceutically acceptable salt thereof for the treatment and/or prevention of muscular or neuromuscular disease. Surprisingly (S)-4-(4-Cyano-2-methoxyphenyl)-5-ethoxy-2,8-dimethyl-1,4-dihydro-1,6-naphthyridin-3-carboxamid according to formula (I) or a pharmaceutically acceptable salt thereof as monotherapy is as effective as a combination of the steroidal MR antagonist spironolactone and the ACE inhibitor lisinopril regarding measurements of grip strength, in base myocardial strain rate, and in improved forces after lengthening contractions of the extensor digitorum longus.

We further identified combinations of non-steroidal mineralocorticoid receptor antagonists in combination with sGC stimulators for the treatment and/or prevention of muscular or neuromuscular disease with synergistic efficacy compared to sGC stimulators or non-steroidal mineralocorticoid receptor antagonists alone. Synergic effects can be found regarding formation of fibrotic tissue, gene expression, heart and muscle damage, muscle function, heart and cardiovascular function, muscle force and/or physical capacity.

We further identified combinations of non-steroidal mineralocorticoid receptor antagonists in combination with sGC activators for the treatment and/or prevention of muscular or neuromuscular disease with synergistic efficacy compared to sGC activators or non-steroidal mineralocorticoid receptor antagonists alone. Synergic effects can be found regarding formation of fibrotic tissue, gene expression, heart and muscle damage, muscle function, heart and cardiovascular function, muscle force and/or physical capacity.

In a combination of sGC stimulators and non-steroidal mineralocorticoid receptor antagonists dosages of the compounds are surprisingly lower compared to sGC stimulators and mineralocorticoid receptor antagonists alone.

In a combination of sGC activators and non-steroidal mineralocorticoid receptor antagonists dosages of the compounds are surprisingly lower compared to sGC activators and mineralocorticoid receptor antagonists alone.

The present invention further provides medicaments which comprise at least one compound or a combination of compounds according to the invention, typically together with one or more inert, nontoxic, pharmaceutically suitable auxiliaries, and the use thereof for the aforementioned purposes.

The compounds, combinations, pharmaceutical compositions and medicaments according to the invention may act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The compounds, combinations, pharmaceutical compositions and medicaments according to the invention can be administered in administration forms suitable for these administration routes.

Suitable administration forms for oral administration are those which work according to the prior art, which release the compounds, combinations, pharmaceutical compositions and medicaments according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/wafers which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/wafers or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral or parenteral administration is preferred, especially oral and intravenous administration.

The compounds, combinations, pharmaceutical compositions and medicaments according to the invention can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dosage is about 0.01 to 100 mg/kg, preferably about 0.01 to 20 mg/kg and most preferably 0.1 to 10 mg/kg of body weight.

For Finerenone administration in the pediatric population a dose of 5 to 40 mg, preferably 10 to 20 mg once daily for children with body weights in the adult range (approximately 70 to 80 kg) is the preferred dosage range.

For children with lower body weights (below 70 to 80 kg) a dose range will be calculated to achieve a similar exposure as observed in adults treated with doses of 5 to 40 mg respectively 10 to 20 mg once daily. (Edginton A N, Schmitt W, Willmann S. *Clin Pharmacokinet.* 2006; 45(10):1013-34).

It may nevertheless be necessary where appropriate to deviate from the stated amounts, specifically as a function of the body weight, route of administration, individual response to the active compound, nature of the preparation and time or interval over which administration takes place. For instance, in some cases, less than the aforementioned minimum amount may be sufficient, while in other cases the upper limit mentioned must be exceeded. In the case of administration of relatively large amounts, it may be advisable to divide these into several individual doses over the course of the day.

Experimental Part

Abbreviations:

Ecc Eccentric contraction het. heterozygous

Hz Hertz ms milliseconds n number (of experimental units)

ND not determined

P/V Pressure/Volume

RT/PCR Reverse transcription polymerase chain reaction

SEM Standard Error of the Mean

Investigation of Therapeutic Efficacy:

For investigations of the effects of non-steroidal MRAs as monotherapy treatment or in combination with sGC stimulators and/or sGC activators, a broad spectrum of in vitro, ex vivo and in vivo tests were used.

Preferentially mice were used, especially transgenic mice (B6.Cg-$^{Terctm1Rdp}$ Dmd$^{mdx-4Cv}$/BlauJ; Jackson Laboratories, strain Nr.: 023535; Dystrophin-deficient, utrophin haploinsufficient (utrn +/−; mdx)). These so called MDX mice carry a mutation in the dystrophin gene which reflects the phenotype and clinical situation of patients with muscular dystrophies (Sacco et al.; *Cell.* 2010 Dec. 23; 143(7):1059-71, Mourkioti et al. *Nat Cell Biol.* 2013 August; 15(8):895-904).

As read-outs were preferentially used:

In vitro, hydroxyproline measurement to assess fibrotic tissue. To analyze the collagen content in tissue samples, hydroxyproline assays were performed. After digestion of the tissue (e.g. heart and muscle) in 6M HCl for three hours at 120° C., chloramine T (0.06 M) was added and samples were mixed and incubated for 20 min at room temperature. 3.15 M perchloric acid and 20% p-dimethylaminobenzaldehyde were added and samples were incubated for additional 20 min at 60° C. The absorbance was determined at 557 nm.

In vitro, semiquantitative RT/PCR (TaqMan PCR) was used to assess gene expression. Mice were euthanized and hearts and muscles (e.g. EDL=extensor digitorum longus muscle, diaphragm) were collected. Total RNA was isolated and gene expression was semiquantified after reverse transcription (RT) reaction via TaqMan polymerase chain reaction (PCR).

In vitro, histopathology to assess heart and muscle damage. Mice were euthanized and hearts and muscles (e.g. EDL, diaphragm) were collected. Cryosections were prepared and stained with Hematoxylin and Eosin (H&E) to assess overall histopathology.

Ex vivo, contractility measurements of muscle contraction in isolated muscles (e.g. EDL, diaphragm) to assess muscle function and contractility. Isolated muscles were stretched to optimal length using twitch contractions (evoked by a single 4 ms pulse). After 10 minutes, a tetanus contraction was performed (150 Hz for 250 ms). After another 5 min rest period, 6 eccentric contractions (150 Hz for 450 ms, subjected to a 3% stretch for the final 200 ms of contraction) were done with two minutes of rest between the first 5 stimulations and 15 minutes of rest between the fifth and sixth stimulation.

In vivo, non-invasive echocardiography and computer tomography to assess heart and cardiovascular function. Mice were anaesthetized and heart structure and function was assessed non-invasively by using the echocardiograph type Vevo2100. In addition, cardiac function was investigated in anesthetized mice by using magnetic resonance imaging (MRI) technique on a 9.4 or 11.7 Tesla 30 mm bore system (Bruker Biospin) together with standard electrocardiographic (ECG). Myocardial strain and strain rate were assessed using vector-based tracking software (Vector Velocity Imaging, Siemens).

In vivo, invasive left-ventricular function and pressure-volume relationship to assess heart and cardiovascular function. Invasive left-ventricular hemodynamics were performed in anaesthetized mice using a pressure catheter and a PN loop catheter.

In vivo assessment of muscle force (Hanging wire test, four limb hanging test, grip strength test) to asses muscle function. For the hanging wire and four limb hanging test, conscious mice are freely hanging on a grid and hanging time is recorded and corrected for body weight of the mice. The grip strength (GS) measurements to investigate front-leg muscle strength were performed in conscious mice by using a grip strength meter (Columbus Instruments). Mice were trained to hold on with their front paws on a wire mesh grid and carefully pulled backwards. This procedure was repeated up to 5 times with one minute breaks between measurements and the maximal power in Newton (N) was registered. The highest grid strength value (GS) in Newton was reported and related to body weight (BW) in mg. All grip strength measurements for each study were conducted by the same investigator to avoid examiner-specific variability and displayed as GS/BW in [N/mg] (Table 1).

In vivo assessment of physical capacity was assessed. Mice were kept in single mouse cages, equipped with running wheels (treadmills) to assess maximal running velocity and running distance.

EXAMPLES

These results show surprisingly that treatment with Finerenone monotherapy is superior to the treatment to a combination of steroidal MR-antagonists with an ACE-Inhibitor (the latter is part of the standard-of-care treatment in DMD) (Lowe et al., *J Neuromuscul Dis.* 2016; 3(3): 395-404, Lowe et al. *J Neuromuscul Dis.* 2018; 5(3):295-306.).

Investigation of Therapeutic Efficacy:

For investigations of the effects of non-steroidal MRAs as monotherapy treatment or in combination with sGC stimulators and/or sGC activators, a broad spectrum of in vitro, ex vivo and in vivo tests were used.

Preferentially mice were used, especially transgenic mice (B6.Cg-Terctm1Rdp Dmdmdx-4Cv/BlauJ; Jackson Laboratories, strain Nr.: 023535). These so called MDX mice carry a mutation in the dystrophin gene which reflects the phenotype and clinical situation of patients with muscular dystrophies. (Sacco et al.; *Cell.* 2010 Dec. 23; 143(7):1059-71, Mourkioti et al. *Nat Cell Biol.* 2013 August; 15(8):895-904).

Grip Strength (GS)/Body Weight (BW) ratio in [N/mg] in WT mice and MDX-mice treated for 16 weeks with either placebo chow, or chow supplemented with 150 ppm sGC stimulator BAY 41-2272, or chow supplemented with 100 ppm non-steroidal MR Antagonist Finerenone. Grip strength determination: Five series of five pulls each with a pause of 1 minute in between the series were performed. The highest value in the first trial was taken as the highest force produced from rested mice and the highest value in the fifth trial was taken as the highest force produced in fatigued mice. These data indicate an improvement of muscle strength after treatment with sGC stimulator BAY 41-2272 alone as well as non-steroidal MR Antagonist Finerenone alone.

The mean of the endocardial circumferential peak of the systolic strain rate determined from the base of the heart (Base_PeakSysSR_Mean (endocardial circumferential S−1)), in WT mice and MDX-mice treated for 16 weeks with either placebo chow, or chow supplemented with 150 ppm

TABLE 1

| | Treatment | | | |
|---|---|---|---|---|
| Groups | Control Mean ± SEM (n) | Untreated Mean ± SEM (n) | BAY41-2272 Mean ± SEM (n) | Finerenone Mean ± SEM (n) |
| Grip Strength trial 1 (N) | 1.5 ± 0.05 (15) | 1.0 ± 0.05 (15) | 1.0 ± 0.04 (17) | 1.1 ± 0.04 (16) |
| GS/BW trial 1 (N/mg) | 58.2 ± 1.5 (15) | 35.2 ± 1.5 (15) | 38.3 ± 1.1 (17) | 40.3 ± 1.0 (16) |
| Grip Strength trial 5 (N) | 1.5 ± 0.05 (15) | 0.8 ± 0.04 (15) | 0.9 ± 0.04 (17) | 1.1 ± 0.04 (16) |
| GS/BW trial 5 (N/mg) | 56.5 ± 1.7 (15) | 29.7 ± 1.1 (15) | 33.9 ± 0.9 (17) | 37.5 ± 1.1 (16) |
| Base_PeakSysSR_Mean (endocardial circumferential S−1) | ND | 0.31 ± 0.03 (12) | 0.36 ± 0.02 (12) | 0.35 ± 0.03 (11) |
| Base_PeakSysSR_Septum (endocardial circumferential S−1) | ND | 0.33 ± 0.03 (12) | 0.39 ± 0.03 (12) | 0.34 ± 0.04 (11) |
| Base_PeakSysSR_Lat (endocardial circumferential S−1) | ND | 0.28 ± 0.03 (12) | 0.37 ± 0.02 (12) | 0.39 ± 0.04 (11) |
| Ecc2 (% Ecc1) | 98 ± 1 (17) | 82 ± 2 (18) | 86 ± 2 (17) | 94 ± 5 (18) |
| Ecc5 (% Ecc1) | 86 ± 2 (17) | 51 ± 4 (18) | 60 ± 5 (17) | 71 ± 7 (18) |
| Post-rest Ecc6 (% Ecc1) | 90 ± 2 (17) | 51 ± 4 (18) | 60 ± 5 (17) | 72 ± 6 (18) | sGC stimulator BAY 41-2272, or chow supplemented with 100 ppm non-steroidal MR Antagonist Finerenone were measured. In Duchenne muscular dystrophy, strain rate reduction indicates myocardial damage. These data indicate an attenuation of heart function decline after treatment with sGC stimulator and non-steroidal MR Antagonist.

EDL eccentric contractions (Ecc) in WT mice and MDX-mice treated for 16 weeks with either placebo chow, or chow supplemented with 150 ppm sGC stimulator BAY 41-2272, or chow supplemented with 100 ppm non-steroidal MR Antagonist Finerenone were measured. This protocol assesses reduced force due to damage and reduced force due to fatigue by comparing excentric-contractions coupling 5 and 6. Reduced force due to the membrane damage seen in dystrophy starts to happen after the first or 2nd eccentric contraction. These data indicate improvement of muscle strength after treatment with sGC stimulator and non-steroidal MR Antagonist.

The invention claimed is:

1. A method for the treatment and/or prevention of Duchenne muscular dystrophy in a human or animal comprising administering a therapeutically effective amount of a non-steroidal mineralocorticoid receptor antagonist that is (4S)-4-(4-cyano-2-methoxyphenyl)-5-ethoxy-2,8-dimethyl-1,4-dihydro-1, 6-naphthyridine-3-carboxamide according to formula (I)

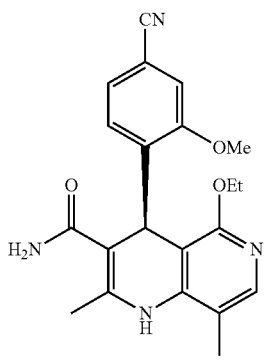

or a pharmaceutically acceptable salt thereof to a human or animal in need thereof.

2. The method of claim 1, further comprising administering to the human or animal an additional therapeutic agent that is an sGC stimulator.

3. The method of claim 2, wherein the sGC stimulator is selected from the group consisting of methyl 4,6-diamino-2-[1-(2-fluorobenzyl)-1H-pyrazolo[3,4-b]pyridin-3-yl]-5-pyrimidinyl(methyl)carbamate, methyl {4,6-diamino-245-fluoro-1-(2-fluorobenzyl)-1H-pyrazolo[3,4-b]pyridine-3-yl]pyrimidin-5-yl}carbamate, 3-(4-amino-5-cyclopropylpyrimidin-2-yl)-1-(2-fluorobenzyl)-1H-pyrazolo[3,4-b]pyridine and 1, 1,1,3,3,3-hexafluoro-2-[({5-fluoro-2-[(2-fluorobenzyl)-5-(1,2-oxazol-3-yl)-1H-pyrazol-3-yl]-4-pyrimidinyl}amino)methyl]-2-propanol or a pharmaceutically acceptable salt thereof.

4. The method of claim 2, wherein the sGC stimulator is 3-(4-amino-5-cyclopropylpyrimidin-2-yl)-1-(2-fluorobenzyl)-1H-pyrazolo[3,4-b]pyridine or a pharmaceutically acceptable salt thereof.

5. The method of claim 1, wherein the non-steroidal mineralocorticoid receptor antagonist is administered at a dose of 5 to 40 mg once daily to a child having a body weight of approximately 70 to 80 kg.

6. The method of claim 5, wherein the non-steroidal mineralocorticoid receptor antagonist is administered at a dose of 10 to 20 mg once daily.

7. The method of claim 2, wherein the non-steroidal mineralocorticoid receptor antagonist is administered at a dose of 5 to 40 mg once daily to a child having a body weight of approximately 70 to 80 kg.

8. The method of claim 7, wherein the non-steroidal mineralocorticoid receptor antagonist is administered at a dose of 10 to 20 mg once daily.

* * * * *